United States Patent
Chassot et al.

(10) Patent No.: US 6,685,751 B2
(45) Date of Patent: *Feb. 3, 2004

(54) SUBSTITUTED 1,4-DIAMINOBENZENE COMPOUNDS AND OXIDATION DYE PRECURSOR COMPOSITIONS CONTAINING SAME

(75) Inventors: Laurent Chassot, Praroman (CH); Hans-Juergen Braun, Ueberstorf (CH)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/251,765

(22) Filed: Sep. 20, 2002

(65) Prior Publication Data

US 2003/0110578 A1 Jun. 19, 2003

Related U.S. Application Data

(63) Continuation of application No. 09/706,000, filed on Nov. 3, 2000, now Pat. No. 6,602,302.

(30) Foreign Application Priority Data

Dec. 18, 1999 (DE) .......................... 199 61 274

(51) Int. Cl.$^7$ ................................. A61K 7/13

(52) U.S. Cl. ...................... 8/405; 8/407; 8/408; 8/409; 8/416; 564/305; 564/336

(58) Field of Search ............................ 8/405, 407, 408, 8/409, 416; 564/305, 336

(56) References Cited

U.S. PATENT DOCUMENTS 3,743,509 A * 7/1973 Evan et al. ................. 96/91 R

* cited by examiner

*Primary Examiner*—Yogendra N. Gupta
*Assistant Examiner*—Eisa Elhilo
(74) *Attorney, Agent, or Firm*—Michael J. Striker

(57) ABSTRACT

New substituted 2,5-diamino-1-aminomethylbenzene compounds of formula (I), or physiologically compatible water-soluble salts thereof,

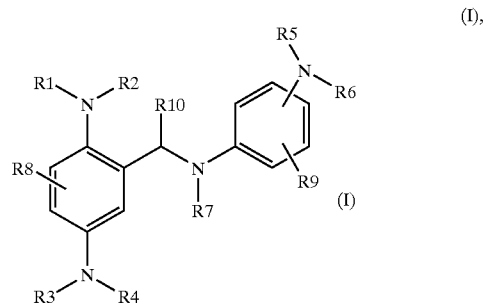

are described as well as methods for preparing them. In addition, oxidation dye precursor compositions for dyeing keratin fibers, especially human hair, which each contain from 0.005 to 20 percent by weight of at least one of the new substituted 2,5-diamino-1-aminomethylbenzene compounds of formula (I), or their physiologically compatible water-soluble salts, are described. Methods for dyeing hair with ready-to-apply dye mixtures made by mixing these oxidation dye precursor compositions with an oxidizing agent, such as hydrogen peroxide solution, are also described.

8 Claims, No Drawings

SUBSTITUTED 1,4-DIAMINOBENZENE COMPOUNDS AND OXIDATION DYE PRECURSOR COMPOSITIONS CONTAINING SAME

CROSS-REFERENCE

This is a continuation of U.S. patent application Ser. No. 09/706,000, filed (Nov. 3, 2000, which has now been assigned U.S. Pat. No. 6,602,302.

BACKGROUND OF THE INVENTION

1. Field of the Invention

The present invention relates to new substituted 2,5-diamino-1-aminomethylbenzene compounds and oxidation dye precursor compositions for dyeing keratin fibers, especially human hair, containing these compounds.

2. Prior Art

Oxidation dyes have been important in the field of dyeing keratin fibers, especially human hair, for a long time. Dyeing occurs by reaction of certain developer substances alone or with certain coupler substances in the presence of a suitable oxidizing agent. It is known from DE-PS 47349 that keratin fibers can be dyed in bright blond to bluish-black color tones by p-phenylenediamine according to the oxidizing agent used. Blue color tones are produced however by a combination of p-phenylenediamine and its derivative compounds with certain coupler substances. Since only compounds that have specifications or properties that, on the one hand, protect the user sufficiently and, on the other hand, produce a stable resistant color that lasts for a sufficient time can be employed, the selection of suitable developer and coupler substances is limited.

SUMMARY OF THE INVENTION

It has now been surprisingly found that certain p-phenylenediamine derivative compounds permit dyeing of keratin fibers, especially human hair, an intense blue color, even without addition of a coupler substance.

Thus intense colors, which are extraordinarily light-fast and wash-fast, are obtained when these p-phenylenediamine derivative compounds are used in an oxidizing medium According to the present invention these p-phenylenedimine derivative compounds are substituted 2,5-diamino-1-aminomethylbenzene compounds of formula (I), or their physiologically compatible water-soluble salts,

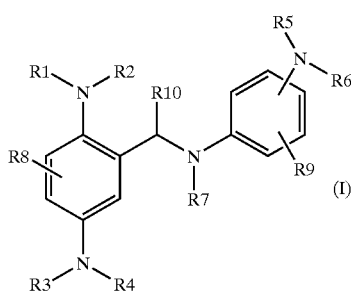

wherein R1, R2, R3, R4, R5, R6 and R7, independently of each other, each represent H, a $C_1$- to $C_6$-alkyl group, a $C_1$- to $C_4$-hydroxyalkyl group, a $C_2$- to $C_4$-dihydroxyalkyl group or a $C_1$- to $C_4$-alkoxy-($C_1$- to $C_2$-)alkyl group or R1 and R2 and/or R3 and R4 and/or R5 and R6 together with the N atom form a four-member to eight-member aliphatic ring, with the proviso that at least two of the groups R1 to R6 each represent hydrogen;

R8 represents hydrogen, a halogen atom, a $C_1$- to $C_4$-alkyl group, a $C_1$- to $C_4$-hydroxyalkyl group or a $C_1$- to $C_4$-alkoxy group;

R9 represents a hydrogen, a halogen atom, a cyano group, a hydroxy group, a $C_1$- to $C_4$-alkoxy group, a $C_1$- to $C_4$-hydroxyalkoxy group, a $C_1$- to $C_6$-alkyl group, a $C_1$- to $C_4$-alkylthioether group; a mercapto group; an amino group, a $C_1$- to $C_4$-alkylamino group, a $C_1$- to $C_4$-hydroxyalkylamino group, a di($C_1$- to $C_4$-alkyl) amino group, a di($C_1$- to $C_4$-hydroxyalkyl)amino group, a {dihydroxy($C_2$- to $C_4$)-alkyl}amino group, a ($C_1$- to $C_4$-hydroxyalkyl)-$C_1$–$C_4$-alkylamino group, a trifluoromethane group, a $C_1$–$C_4$-hydroxyalkyl group or a $C_3$–$C_4$ dihydroxyalkyl group; and R10 represents hydrogen or a $C_1$- to $C_6$-alkyl group.

For example, the following compounds of formula (I) can be named as examples:
2-((2-amino-phenylamino)-methyl)-1,4-diaminobenzene; 2-((2-bis(hydroxyethyl)amino-phenylamino)-methyl)-1,4-diaminobenzene; 2-((2-dimethylaminophenylamino)-methyl)-1,4-diaminobenzene; 2-((3-aminophenylamino)methyl)-1,4-diaminobenzene; 2-((3-bis(hydroxyethyl)aminophenylamino)methyl)-1,4-diaminobenzene; 2-((3-dimethylaminophenylamino)-methyl)-1,4-diaminobenzene; 2-((4-amino-phenylamino)methyl)-1,4-diaminobenzene; 2-((4-bis-(hydroxyethyl)aminophenylamino)methyl)-1,4-diaminobenzene; 2-((4-dimethylamino-phenylamino)methyl)-1,4-diaminobenzene; $N^1,N^1$-bis(hydroxyethyl)-2-((2-aminophenylamino)methyl)-1,4-diaminobenzene; $N^1,N^1$-bis(hydroxyethyl)-2-((2-bis(hydroxyethyl)aminophenylamino)-methyl)-1,4-diaminobenzene; $N^1,N^1$-bis-(hydroxyethyl)-2-((2-dimethylaminophenylamino)-methyl)-1,4-diaminobenzene; $N^1,N^1$-bis(hydroxyethyl)-2-((3-amino-phenylamino)-methyl)-1,4-diaminobenzene; $N^1,N^1$-bis(hydroxyethyl)-2-((3-bis(hydroxyethyl)aminophenylamino)-methyl)-1,4-diaminobenzene, $N^1,N^1$-bis(hydroxyethyl)-2-((3-dimethylamino-phenylamino)-methyl)-1,4-diaminobenzene; $N^1,N^1$-bis(hydroxyethyl)-2-((4-amino-phenylamino)-methyl)-1,4-diaminobenzene; $N^1,N^1$-bis(hydroxyethyl)-2-((4-bis(hydroxyethyl)aminophenylamino)methyl)-1,4-diaminobenzene; $N^1,N^1$-bis(hydroxyethyl)-2-((4-dimethylamino-phenylamino)-methyl)-1,4-diaminobenzene; $N^1$-dihydroxypropyl-2-((2-amino-phenylamino)-methyl)-1,4-diaminobenzene; $N^1$-dihydroxypropyl-2-((2-bis(hydroxyethyl)aminophenylamino)-methyl)-1,4-diaminobenzene; $N^1$-dihydroxypropyl-2-((2-dimethylaminophenylamino)-methyl)-1,4-diaminobenzene; $N^1$-dihydroxypropyl-2-((3-amino-phenylamino)-methyl)-1,4-diaminobenzene; $N^1$-dihydroxypropyl-2-((3-bis-(hydroxyethyl)aminophenylamino)-methyl)-1,4-diaminobenzene; $N^1$-dihydroxypropyl-2-((3-dimethylaminophenylamino)-methyl)-1,4-diaminobenzene; $N^1$-dihydroxypropyl-2-((4-amino-phenylamino)-methyl)-1,4-diaminobenzene; $N^1$-dihydroxypropyl-2-((4-bis(hydroxyethyl)amino-phenylamino)-methyl)-1,4-diaminobenzene; $N^1$-dihydroxypropyl-2-((4-dimethylamino-phenylamino)methyl)-1,4-diaminobenzene; $N^1$-hydroxyethyl-2-((2-aminophenylamino)-methyl)-1,4-diaminobenzene; $N^1$-hydroxyethyl-2-((2-bis(hydroxyethyl)aminophenylamino)-methyl)-1,4-diaminobenzene;

$N^1$-hydroxyethyl-2-((2-dimethylamino-phenylamino)-methyl)-1,4-diaminobenzene; $N^1$-hydroxyethyl-2-((3-amino-phenylamino)-methyl)-1,4-diaminobenzene; $N^1$-hydroxyethyl-2-((3-bis(hydroxyethyl)aminophenylamino)methyl)-1,4-diaminobenzene; $N^1$-hydroxyethyl-2-((3-dimethylaminophenylamino)methyl)-1,4-diaminobenzene; $N^1$-hydroxyethyl-2-((4-aminophenylamino)-methyl)-1,4-diaminobenzene; $N^1$-hydroxyethyl-2-((4-bis(hydroxyethyl)-aminophenylamino)-methyl)-1,4-diaminobenzene; $N^1$-hydroxyethyl-2-((4-dimethylamino-phenylamino)-methyl)-1,4-diaminobenzene; $N^4$ $N^4$-bis(hydroxyethyl)-2-((2-amino-phenylamino)-methyl)-1,4-diaminobenzene; $N^4,N^4$-bis-(hydroxyethyl)-2-((2-bis(hydroxyethyl)aminophenylamino)-methyl)-1,4-diaminobenzene; $N^4,N^4$-bis(hydroxyethyl)-2-((2-dimethylamino-phenylamino)-methyl)-1,4-diaminobenzene; $N^4$ $N^4$-bis(hydroxyethyl)-2-((3-aminophenylamino)-methyl)-1,4-diaminobenzene; $N^4,N^4$-bis(hydroxyethyl)-2-((3-bis(hydroxyethyl)aminophenylamino)methyl)-1,4-diaminobenzene; $N^4,N^4$-bis(hydroxyethyl)-2-((3-dimethylamino-phenylamino)-methyl)-1,4-diaminobenzene; $N^4$ $N^4$-bis(hydroxyethyl)-2-((4-amino-phenylamino)-methyl)-1,4-diaminobenzene; $N^4,N^4$-bis-(hydroxyethyl)-2-((4-bis(hydroxyethyl)aminophenylamino)methyl)-1,4-diaminobenzene; $N^4$ $N^4$-bis(hydroxyethyl)-2-((4-dimethylamino-phenylamino)-methyl)-1,4-diaminobenzene; $N^4$-dihydroxypropyl-2-((2-aminophenylamino)-methyl)-1,4-diaminobenzene; $N^4$-dihydroxypropyl-2-((2-bis(hydroxyethyl)amino-phenylamino)-methyl)-1,4-diaminobenzene-$N^4$-dihydroxypropyl-2-((2-dimethylaminophenylamino)methyl)-1,4-diaminobenzene; $N^4$-dihydroxypropyl-2-((3-aminophenylamino)-methyl)-1,4-diaminobenzene; $N^4$-dihydroxypropyl-2-((3-bis-(hydroxyethyl)aminophenylamino)-methyl)-1,4-diaminobenzene; $N^4$-dihydroxypropyl-2-((3-dimethylaminophenylamino)-methyl)-1,4-diaminobenzene; $N^4$-dihydroxypropyl-2-((4-amino-phenylamino)-methyl)-1,4-diaminobenzene; $N^4$-dihydroxypropyl-2-((4-bis(hydroxyethyl)amino-phenylamino)-methyl)-1,4-diaminobenzene; $N^4$-dihydroxypropyl-2-((4-dimethylaminophenylamino)methyl)-1,4-diaminobenzene; $N^4$-hydroxyethyl-2-((2-aminophenylamino)methyl)-1,4-diaminobenzene, $N^4$-hydroxyethyl-2-((2-bis(hydroxyethyl)amino-phenyl-amino)-methyl)-1,4-diaminobenzene; $N^4$-hydroxyethyl-2-((2-dimethylaminophenylamino)-methyl)-1,4-diaminobenzene; $N^4$-hydroxyethyl-2-((3-aminophenylamino)methyl)-1,4-diaminobenzene; $N^4$-hydroxyethyl-2-((3-bis(hydroxyethyl)amino-phenylamino)methyl)-1,4-diaminobenzene; $N^4$-hydroxyethyl-2-((3-dimethylaminophenylamino)methyl)-1,4-diaminobenzene; $N^4$-hydroxyethyl-2-((4-aminophenylamino)-methyl)-1,4-diaminobenzene; $N^4$-hydroxyethyl-2-((4-bis(hydroxyethyl)amino-phenylamino)-methyl)-1,4-diaminobenzene; $N^4$-hydroxyethyl-2-((4-dimethylamino-phenylamino)-methyl)-1,4-diaminobenzene; 2-((2-(dihydroxypropyl)amino-phenylamino)-methyl)-1,4-diaminobenzene; 2-((2-(pyrrolidin-1-yl)-phenylamino)-methyl)-1,4-diaminobenzene; 2-((2-hydroxyethylamino-phenylamino)-methyl)-1,4-diaminobenzene; 2-((2-methylamino-phenylamino)-methyl)-1,4-diaminobenzene; 2-((3-(dihydroxypropyl)amino-phenylamino)-methyl)-1,4-diaminobenzene; 2-((3-(pyrrolidin-1-yl)-phenylamino)-methyl)-1,4-diaminobenzene; 2-((3-hydroxyethylamino-phenylamino)-methyl)-1,4-diaminobenzene, 2-((3-methylamino-phenylamino)-methyl)-1,4-diaminobenzene; 2-((4-(dihydroxypropyl)amino-phenylamino)-methyl)-1,4-diaminobenzene-2-((4-(pyrrolidin-1-yl)-phenylamino)-methyl)-1,4-diaminobenzene; 2-((4-hydroxyethylamino-phenylamino)-methyl)-1,4-diaminobenzene; 2-((4-methylamino-phenylamino)-methyl)-1,4-diaminobenzene; 2-((methyl-(2-(dihydroxypropylamino)-phenyl)-amino)-methyl)-1,4-diaminobenzene; 2-((methyl-(2-amino-phenyl)-amino)-methyl)-1,4-diaminobenzene; 2-((methyl-(2-bis(hydroxyethyl)amino-phenyl)-amino)-methyl)-1,4-diaminobenzene; 2-((methyl-(3-(dihydroxypropylamino)-phenyl)-amino)-methyl)-1,4-diaminobenzene; 2-((methyl-(3-amino-phenyl)-amino)-methyl)-1,4-diaminobenzene; 2-((methyl-(3-bis(hydroxyethyl)amino-phenyl)-amino)-methyl)-1,4-diaminobenzene; 2-((methyl-(4-(dihydroxypropylamino)-phenyl)-amino)methyl)-1,4-diaminobenzene; 2-((methyl-(4-amino-phenyl)-amino)-methyl)-1,4-diaminobenzene; 2-((methyl-(4-bis(hydroxyethyl)amino-phenyl)-amino)-methyl)-1,4-diaminobenzene; 2-((1-(2-amino-phenyl)-amino)-ethyl)-1,4-diaminobenzene; 2-((1-(2-bis(hydroxyethyl)amino-phenyl)-amino)-ethyl)-1,4-diaminobenzene; 2-((1-(2-dimethylamino-phenyl)-amino)-ethyl)-1,4-diaminobenzene; 2-((1-(3-aminophenyl)-amino)-ethyl)-1,4-diaminobenzene; 2-((1-(3-bis(hydroxyethyl)amino-phenyl)-amino)-ethyl)-1,4-diaminobenzene; 2-((1-(3-dimethylamino-phenyl)-amino)-ethyl)-1,4-diaminobenzene; 2-((1-(4-amino-phenyl)-amino)-ethyl)-1,4-diaminobenzene; 2-((1-(4-bis(hydroxyethyl)amino-phenyl)-amino)-ethyl)-1,4-diaminobenzene; 2-((1-(4-dimethylamino-phenyl)-amino)-ethyl)-1,4-diaminobenzene; 2-((2-((2,3-diamino-phenylamino)-methyl)-1,4-diaminobenzene; 2-((2-((2,4-diamino-phenylamino)-methyl)-1,4-diaminobenzene; 2-((2-((3,4-diamino-phenylamino)-methyl)-1,4-diaminobenzene; 2-((methyl-(2,3-diamino-phenyl)-amino)-methyl)-1,4-diaminobenzene; 2-((methyl-(2,4-diamino-phenyl)-amino)-methyl)-1,4-diaminobenzene; 2-((methyl-(3,4-diamino-phenyl)-amino)-methyl)-1,4-diaminobenzene; 2-(1-(2,3-diamino-phenylamino)-ethyl)-1,4-diaminobenzene; 2-(1-(2,4-diamino-phenylamino)-ethyl)-1,4-diaminobenzene; 2-(1-(3,4-diamino-phenylamino)-ethyl)-1,4-diaminobenzene; 2-((2-(2-hydroxyethoxy)-4-amino-phenylamino)-methyl)-1,4-diaminobenzene; 2-((2-(2-hydroxyethyl)-4-amino-phenylamino)-methyl)-1,4-diaminobenzene; 2-((2-chloro-4-amino-phenylamino)-methyl)-1,4-diaminobenzene; 2-((2-hydroxy-4-amino-phenylamino)-methyl)-1,4-diaminobenzene; 2-((2-methoxy-4-amino-phenylamino)-methyl)-1,4-diaminobenzene; 2-((2-methyl-4-amino-phenylamino)-methyl)-1,4-diaminobenzene; 2-((3-(2-hydroxyethoxy)-4-amino-phenylamino)-methyl)-1,4-diaminobenzene; 2-((3-(2-hydroxyethyl)-4-amino-phenylamino)-methyl)-1,4-diaminobenzene; 2-((3-chloro-4-amino-phenylamino)-methyl)-1,4-diaminobenzene; 2-((3-hydroxy-4-amino-phenylamino)-methyl)-1,4-diaminobenzene; 2-((3-methoxy-4-amino-phenylamino)-methyl)-1,4-diaminobenzene; 2-((3-methyl-4-amino-phenylamino)-methyl)-1,4-diaminobenzene; 2-((2-(2-hydroxyethoxy)-3-amino-phenylamino)-methyl)-1,4-diaminobenzene; 2-((2-(2-hydroxyethyl)-3-amino-phenylamino)-methyl)-

1,4-diaminobenzene; 2-((2-chloro-3-amino-phenylamino)-methyl)-1,4-diaminobenzene; 2-((2-hydroxy-3-amino-phenylamino)-methyl)-1,4-diaminobenzene; 2-((2-methyl-3-amino-phenylamino)-methyl)-1,4-diaminobenzene; 2-((4-(2-hydroxyethoxy)-3-amino-phenylamino)-methyl)-1,4-diaminobenzene; 2-((4-(2-hydroxyethyl)-3-amino-phenylamino)-methyl)-1,4-diaminobenzene; 2-((4-chloro-3-amino-phenylamino)-methyl)-1,4-diaminobenzene; 2-((4-hydroxy-3-amino-phenylamino)-methyl)-1,4-diaminobenzene; 2-((4-methyl-3-amino-phenylamino)-methyl)-1,4-diaminobenzene; 2-((5-(2-hydroxyethoxy)-3-amino-phenylamino)-methyl)-1,4-diaminobenzene; 2-((5-(2-hydroxyethyl)-3-amino-phenylamino)-methyl)-1,4-diaminobenzene; 2-((5-chloro-3-amino-phenylamino)-methyl)-1,4-diaminobenzene; 2-((5-hydroxy-3-amino-phenylamino)-methyl)-1,4-diaminobenzene; 2-((5-methyl-3-amino-phenylamino)-methyl)-1,4-diaminobenzene; 2-((6-(2-hydroxyethoxy)-3-amino-phenylamino)-methyl)-1,4-diaminobenzene; 2-((6-(2-hydroxyethyl)-3-amino-phenylamino)-methyl)-1,4-diaminobenzene; 2-((6-chloro-3-amino-phenylamino)-methyl)-1,4-diaminobenzene; 2-((6-hydroxy-3-amino-phenylamino)-methyl)-1,4-diaminobenzene; 2-((6-methyl-3-amino-phenylamino)-methyl)-1,4-diaminobenzene; 2-((3-(2-hydroxyethoxy)-2-amino-phenylamino)-methyl)-1,4-diaminobenzene; 2-((3-(2-hydroxyethyl)-2-amino-phenylamino)-methyl)-1,4-diaminobenzene; 2-((3-chloro-2-amino-phenylamino)-methyl)-1,4-diaminobenzene; 2-((3-hydroxy-2-amino-phenylamino)-methyl)-1,4-diaminobenzene; 2-((3-methoxy-2-amino-phenylamino)-methyl)-1,4-diaminobenzene; 2-((3-methyl-2-amino-phenylamino)-methyl)-1,4-diaminobenzene; 2-((4-(2-hydroxyethoxy)-2-amino-phenylamino)-methyl)-1,4-diaminobenzene; 2-((4-(2-hydroxyethyl)-2-amino-phenylamino)-methyl)-1,4-diaminobenzene; 2-((4-chloro-2-amino-phenylamino)-methyl)-1,4-diaminobenzene; 2-((4-hydroxy-2-amino-phenylamino)-methyl)-1,4-diaminobenzene; 2-((4-methoxy-2-amino-phenylamino)-methyl)-1,4-diaminobenzene; 2-((4-methyl-2-amino-phenylamino)-methyl)-1,4-diaminobenzene; 2-((5-(2-hydroxyethoxy)-2-amino-phenylamino)-methyl)-1,4-diaminobenzene; 2-((5-(2-hydroxyethyl)-2-amino-phenylamino)-methyl)-1,4-diaminobenzene; 2-((5-chloro-2-amino-phenylamino)-methyl)-1,4-diaminobenzene; 2-((5-hydroxy-2-amino-phenylamino)-methyl)-1,4-diaminobenzene; 2-((5-methoxy-2-amino-phenylamino)-methyl)-1,4-diaminobenzene; 2-((5-methyl-2-amino-phenylamino)-methyl)-1,4-diaminobenzene; 2-((6-(2-hydroxyethoxy)-2-amino-phenylamino)-methyl)-1,4-diaminobenzene; 2-((6-(2-hydroxyethyl)-2-amino-phenylamino)-methyl)-1,4-diaminobenzene; 2-((6-chloro-2-amino-phenylamino)-methyl)-1,4-diaminobenzene; 2-((6-hydroxy-2-amino-phenylamino)-methyl)-1,4-diaminobenzene; 2-((6-methoxy-2-amino-phenylamino)-methyl)-1,4-diaminobenzene; 2-((6-methyl-2-amino-phenylamino)-methyl)-1,4-diaminobenzene.

Compounds of formula (I) are preferred, in which (i) $R_1$, $R_2$, $R_3$ and $R_4$ are each hydrogen and/or (ii) one or more of the groups $R_5$ to $R_{10}$ are each hydrogen and/or (iii) $R_5$ and $R_6$, independently of each other, are hydrogen, a methyl group or a $C_1$- to $C_4$-hydroxyalkyl group or (iv) $R_7$, $R_8$, $R_9$ and $R_{10}$ are each hydrogen and $R_5$ and $R_6$ are, independently of each other, hydrogen, a $C_1$- to $C_4$-alkyl group, a $C_1$- to $C_4$-hydroxyalkyl group or a $C_2$- to $C_4$-dihydroxyalkyl group or $R_5$ and $R_6$ together with the N atom form a four-member ring.

The following compounds of formula (I) are particularly preferred: 2-((2-amino-phenylamino)-methyl)-1,4-diaminobenzene; 2-((3-aminophenylamino)-methyl)-1,4-diaminobenzene; 2-((4-amino-phenylamino)methyl)-1,4-diaminobenzene; 2-((4-bis(2-hydroxyethyl)amino-phenylamino)-methyl)-1,4-diaminobenzene; 2-((4-dimethylamino-phenylamino)methyl)-1,4-diaminobenzene; $N^1,N^1$-bis(hydroxyethyl)-2-((3-aminophenylamino)-methyl)-1,4-diaminobenzene; $N^1,N^1$-bis(hydroxyethyl)-2-((4-amino-phenylamino)-methyl)-1,4-diaminobenzene; $N^1,N^1$-bis(hydroxyethyl)-2-((4-bis(2-hydroxyethyl)aminophenylamino)-methyl)-1,4-diaminobenzene; $N^1$-dihydroxypropyl-2-((4-amino-phenylamino)-methyl)-1,4-diaminobenzene; $N^1$-dihydroxypropyl-2-((4-bis(2-hydroxyethyl)amino-phenylamino)methyl)-1,4-diaminobenzene; $N^1$-dihydroxypropyl-2-((4-dimethylamino-phenylamino)-methyl)-1,4-diaminobenzene; $N^4,N^4$-bis(hydroxyethyl)-2-((3-aminophenylamino)-methyl)-1,4-diaminobenzene; $N^4,N^4$-bis(hydroxyethyl)-2-((4-amino-phenylamino)-methyl)-1,4-diaminobenzene; $N^4,N^4$-bis(hydroxy-ethyl)-2-((4-bis(2-hydroxyethyl)amino-phenylamino)-methyl)-1,4-diaminobenzene; $N^4,N^4$-bis(hydroxyethyl)-2-((4-dimethylamino-phenylamino)-methyl)-1,4-diaminobenzene; $N^4$-dihydroxypropyl-2-((4-amino-phenylamino)-methyl)-1,4-diaminobenzene; $N^4$-dihydroxypropyl-2-((4-bis(2-hydroxyethyl)amino-phenylamino)-methyl)-1,4-diaminobenzene; $N^4$-dihydroxypropyl-2-((4-dimethylamino-phenylamino)-methyl)-1,4-diaminobenzene; 2-((2-(2-hydroxyethyl)amino-phenylamino)-methyl)-1,4-diaminobenzene; 2-((2-(pyrrolidin-1-yl)-phenylamino)-methyl)-1,4-diaminobenzene; 2-((2-dihydroxypropylamino-phenylamino)-methyl)-1,4-diaminobenzene; 2-((2-methylamino-phenylamino)-methyl)-1,4-diaminobenzene; 2-((3-(2-hydroxyethyl)amino-phenylamino)-methyl)-1,4-diaminobenzene; 2-((3-(pyrrolidin-1-yl)-phenylamino)-methyl)-1,4-diaminobenzene; 2-((3-dihydroxypropylamino-phenylamino)-methyl)-1,4-diaminobenzene; 2-((3-methylamino-phenylamino)-methyl)-1,4-diaminobenzene; 2-((4-(2-hydroxyethyl)amino-phenylamino)-methyl)-1,4-diaminobenzene; 2-((4-(pyrrolidin-1-yl)-phenylamino)-methyl)-1,4-diaminobenzene; 2-((4-dihydroxypropylamino-phenylamino)-methyl)-1,4-diaminobenzene; 2-((4-methylamino-phenylamino)-methyl)-1,4-diaminobenzene; 2-((2-(2-hydroxyethyl)-4-amino-phenylamino)-methyl)-1,4-diaminobenzene; 2-((2-(2-hydroxyethyl)-4-bis(2-hydroxyethyl)amino-phenylamino)-methyl)-1,4-diaminobenzene; 2-((2-chloro-4-amino-phenylamino)-methyl)-1,4-diaminobenzene; 2-((2-chloro-4-bis(2-hydroxyethyl)amino-phenylamino)-methyl)-1,4-diaminobenzene; 2-((2-methoxy-4-amino-phenylamino)-methyl)-1,4-diaminobenzene; 2-((2-methoxy-4-bis(2-hydroxyethyl)aminophenylamino)-methyl)-1,4-diaminobenzene; 2-((2-methyl-4-aminophenylamino)-methyl)-1,4-diaminobenzene; 2-((2-methyl-4-bis(2-hydroxyethyl)amino-phenylamino)-methyl)-1,4-diaminobenzene; 2-((3-(2-hydroxyethyl)-4-amino-phenylamino)-methyl)-1,4-diaminobenzene, 2-((3-(2-hydroxyethyl)-4-bis(2-hydroxyethyl)amino-phenylamino)-methyl)-1,4-diaminobenzene; 2-((3-chloro-4-amino-phenylamino)-methyl)-1,4-diaminobenzene; 2-((3-chloro-4-bis(2-hydroxyethyl)amino-phenylamino)-methyl)-1,4-diaminobenzene; 2-((3-methoxy-4-amino-phenylamino)-methyl)-1,4-diaminobenzene; 2-((3-methoxy-4-bis(2-hydroxyethyl)aminophenylamino)-methyl)-1,4-diaminobenzene; 2-((3-methyl-4-aminophenylamino)- methyl)-1,4-diaminobenzene; 2-((3-methyl-4-bis(2-hydroxyethyl)amino-phenylamino)-methyl)-1,4-diaminobenzene; 2-((4-(2-hydroxyethoxy)-3-aminophenylamino)-methyl)-1,4-diaminobenzene; 2-((4-(2-hydroxyethoxy)-3-bis(2-hydroxyethyl)amino-phenylamino)-methyl)-1,4-diaminobenzene; 2-((4-(2-hydroxyethyl)-3-aminophenylamino)-methyl)-1,4-diaminobenzene and 2-((4-(2-hydroxyethyl)-3-bis(2-hydroxyethyl)amino-phenylamino)-methyl)-1,4-diaminobenzene.

The compounds of formula (I) can be used both as free bases and also in the form of their physiologically compatible salts with inorganic or organic acids, for example with hydrochloric acid, sulfuric acid, phosphoric acid, acetic acid, propionic acid, lactic acid or citric acid.

The manufacture of the substituted 2,5-diamino-1-aminomethylbenzene compounds of formula (I) can take place using known synthetic methods. The synthesis of the compounds of the invention, for example, can be performed as follows: either a) by reductive amination of a substituted benzene compound of formula (II):

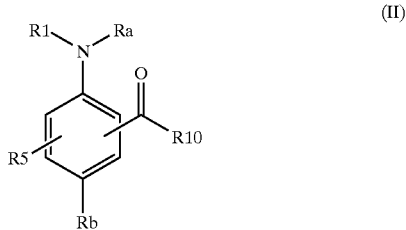

(II)

with an amine of formula (III) and subsequent splitting off of the protective group;

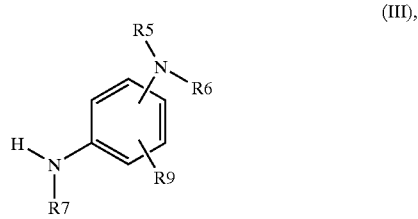

(III), wherein the R groups in formula (II) and (III) have the following significance.

Ra represents a protective group, such as described, for example, in the chapter "Protective Groups in Organic Synthesis", Chapter 7, Wiley Interscience, 1991;
Rb represents NR1Ra or NR1R2, while
X, R1, R2, R5, R6, R7, R9 and R10 have the same significance as in formula (I); or b) by substitution of a substituted benzene compound of formula (IV)

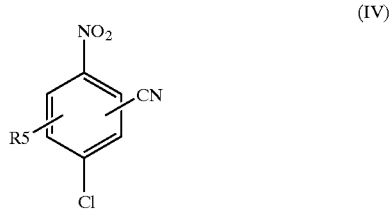

(IV)

with an amine of formula HNR1 R2, reduction of the nitrile group, alkylation of the amino group with a compound of formula (V) and subsequent reduction of the nitrile group;

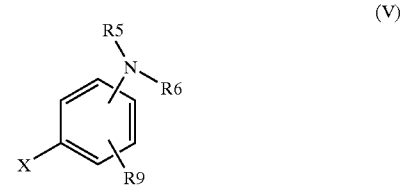

(V)

wherein in formula (IV) and (V) X represents a halogen atom and R1, R2, R5, R6 and R9 have the same significance as in formula (I).

The substituted 2,5-diamino-1-aminomethylbenzene compounds of formula (I) are soluble in water and provide colors with higher color intensity or depth and outstanding color fastness, especially light fastness, wash fastness and rubbing fastness The subject matter of the present invention also includes oxidation dye precursor compositions for oxidative dyeing of keratin fibers, which necessarily contain at least one of the substituted 2,5-diamino-1-aminomethylbenzene compounds of formula 1.

These oxidation dye precursor compositions according to the invention contain about 0.005 to 20, preferably from 0.01 to 10, percent by weight of the substituted 2,5-diamino-1-aminomethylbenzene compound of formula 1. A content of from 0.10 to 8 percent by weight of the substituted 2,5-diamino-1-aminomethylbenzene compound of formula (I) is especially preferred.

The compounds of formula (I) dye keratinic material in intense blue color shades when other dyestuffs are not present. To obtain other color shades additional oxidation dyestuffs, for example developer substances or coupler substances, can be used alone or in mixture with each other, together with at least one compound of formula (I).

Preferred coupler compounds for use with the compounds of formula (I) in the compositions according to the invention include 2,6-diaminopyridine, 2-amino-4-[(2-hydroxyethyl)amino]-anisole, 2,4-diamino-1-fluoro-5-methylbenzene, 2,4-diamino-1-methoxy-5-methylbenzene, 2,4-diamino-1-ethoxy-5-methylbenzene, 2,4-di amino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)-benzene, 2,4-diamino-1,5-di(2-hydroxyethoxy)-benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)-amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)-amino]aniline, 1,3-di(2,4-diaminophenoxy)propane, di(2,4-diaminophenoxy)-methane, 1,3-diamino-2,4-dimethoxybenzene, 2,6-bis-(2-hydroxyethyl)amino-toluene, 4-hydroxyindole, 3-dimethylaminophenol, 3-diethylaminophenol, 5-amino-2-methylphenol, 5-amino-4-fluoro-2-methyl phenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)

amino]-2-methylphenol, 3-[(2-hydroxyethyl) amino]phenol, 3-[(2-methoxyethyl)amino]-phenol, 5-amino-2-ethylphenol, 2-(4-amino-2-hydroxy-phenoxy)ethanol, 5-[(3-hydroxypropyl)amino]-2-methylphenol, 3-[(2,3-dihydroxypropyl) amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methyl-benzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolindione.

Preferred developer compounds for use with the compounds of formula (I) in the compositions of the invention include 1,4-diaminobenzene; 1,4-diamino-2-methylbenzene; 1,4-diamino-2,6-dimethylbenzene; 2,5-diamino-1,3-diethylbenzene dihydrochloride; 1,4-diamino-2,5-dimethylbenzene; 1,4-diamino-2,3-dimethylbenzene; 2-chloro-1,4-diamino-benzene; 1,4-diamino-2-(thiophen-2-yl)benzene dihydrochloride; 1,4-diamino-2-(thiophen-3-yl) benzene dihydrochloride; 3-(2,5-diaminophenyl)pyridine trihydrochloride; 2,5-diaminobiphenyl dihydrochloride; 1,4-diamino-2-(methoxy-methyl)benzene dihydrochloride; 1-(aminomethyl)-2,5-diaminobenzene-dihydrochloride; 1,4-diamino-2-(hydroxymethyl)benzene; 1,4-diamino-2-(2-hydroxyethoxy)-benzene dihydrochloride; 2-(2-(acetylamino)ethoxy)-1,4-diamino-benzene dihydrochloride; 4-phenylaminoaniline; 4-dimethylaminoaniline; 4-(dipropylamino)aniline; 4-diethylaminoaniline; 4-(ethyl (2-hydroxyethyl)amino)-aniline; 4-(di(2-hydroxyethyl) amino)-aniline; 4-(di(2-hydroxyethyl)amino)-2-methylaniline; 4-((2-methoxyethyl)amino)-aniline; 4-((3-hydroxypropyl)amino)-aniline; 4-((2,3-dihydroxypropyl) amino)aniline; 1,4-diamino-2-(2-hydroxyethyl)-benzene; 1,4-diamino-2-(1-methylethyl)benzene; 1,3-bis-((4-aminophenyl)-(2-hydroxyethyl)amino)-2-propanol; 1,4-di ((4-aminophenyl)amino)butane; 1,8-bis-(2,5-diaminophenoxy)-3,6-dioxaoctane; 4-aminophenol; 4-amino-3-methylphenol; 4-amino-3-(hydroxymethyl) phenol; 4-amino-3-fluorophenol; 4-methylaminophenol; 4-amino-2-(aminomethyl)-phenol; 4-amino-2-(hydroxymethyl)phenol; 4-amino-2-fluorophenol; 4-amino-2-((2-hydroxyethyl)amino)-methylphenol; 4-amino-2-methylphenol; 4-amino-2-(methoxymethyl)phenol; 4-amino-2-(2-hydroxyethyl)-phenol; 5-aminosalicylic acid; 2,5-diaminopyridine; 2,4,5,6-tetraminopyrimidine; 2,5,6-triamino-4(1H)-pyrimidone; 4,5-diamino-1-(2-hydroxyethyl)-1H-pyrazole; 4,5-diamino-1-(1-methylethyl)-1H-pyrazole; 4,5-diamino-1-((4-methylphenyl)methyl)-1H-pyrazole; 1-((4-chlorophenyl) methyl)-4,5-diamino-1H-pyrazole and 4,5-diamino-1-methyl-1H-pyrazole.

The oxidation dye precursor compositions according to the invention can also contain additional dye compounds, for example 2-aminophenol, 2-amino-6-methylphenol and 2-amino-5-methylphenol, as well as other direct-dyeing dye compounds, such as triphenylmethane dye compounds, for example 4-[(4'-aminophenyl)-(4'-imino-2",5"-cyclohexadien-1"-yliden)-methyl]-2-methylaminobenzene monohydrochloride (C.I. 42 510) and 4-[(4'-amino-3'-methylphenyl)-(4"-imino-3"-methyl-2",5"cyclohexadien-1"-yliden)-methyl]-2-methylaminobenzene monohydrochloride (C.I. 42 520); aromatic nitro dye compounds, such as 4-(2'-hydroxyethyl)amino-nitrotoluene, 2-amino-4,6-dinitrophenol, 2-amino-5-(2'-hydroxyethyl)amino-nitrobenzene, 2-chloro-6-(ethyl-amino)-4-nitrophenol, 4-chloro-N-(2-hydroxyethyl)-2-nitroaniline, 5-chloro-2-hydroxy-4-nitroaniline, 2-amino-4-chloro-6-nitrophenol and 1-[(2'-ureidoethyl)-amino-4-nitrobenzene; azo dye compounds, for example 6-[(4'-aminophenyl)-azo]-5-hydroxy-naphthalene-1-sulfonic acid sodium salt (C.I. 14 805) and dispersion dye compounds, such as 1,4-diaminoanthraquinone and 1,4,5,8-tetra-aminoanthraquinone. The compositions according to the invention can contain these additional dye compounds in amounts of about 0.1 to 4.0 percent by 20 weight. For example, it is possible to obtain blond to brown hair colors using a combination of the compounds of formula (I) with 2-aminophenol, 2-amino-6-methylphenol or 2-amino-5-methylphenol Understandably the coupler compounds and developer compounds as well as the other dye compounds, in so far as they are bases, may be used in the form of their physiologically compatible salts with organic or inorganic acids, such as hydrochloric or sulfuric acid. In so far as they have aromatic OH groups they may be used in the form of salts with bases, for example as alkali metal phenolates.

Furthermore in the case of oxidation hair dye precursor compositions, used for dyeing hair, still other conventional cosmetic additives may be included in the compositions. These conventional cosmetic additive ingredients include, for example, antioxidants such as ascorbic acid, thioglycolic acid or sodium sulfite, as well as perfume oils, complex formers, wetting agents, emulsifiers, thickeners and care materials. The form of these preparations containing the dyeing agents according to the invention can, for example, be a solution, especially an aqueous or aqueous-alcoholic solution. However the forms of the preparation according to the invention that are particularly preferred include a cream, a gel and an emulsion. These preparations comprise a mixture of the dye compounds according to the invention together with the conventional cosmetic additive suitable for these preparations.

Conventional additive ingredients for the solutions, creams, emulsions or gels include, for example, solvents, such as water, lower aliphatic alcohols, such as ethanol, propanol or isopropanol, glycerol or glycols, such as 1,2-propylene glycol; wetting agents or emulsifiers from the classes of anionic surfactants, cationic surfactants, amphoteric surfactants and nonionic surfactants, such as fatty alcohol sulfates, ethoxylated fatty alcohol sulfates, alkyl sulfonates, alkylbenzene sulfonates, alkyltrimethyl ammonium salts, alkylbetaines, ethoxylated fatty alcohols, ethoxylated nonylphenols, fatty acid alkanol amides and ethoxylated fatty acid esters; thickeners, such as higher fatty alcohols, starches, cellulose derivatives, petrolatum, paraffin oils and fatty acids; as well as care materials, such as cationic resins, lanolin derivative compounds, cholesterol, pantothenic acid and betaine. The above-mentioned additive ingredients are used in amounts suitable for their purposes, for example the wetting agents and emulsifiers in concentrations of about 0.5 to 30 percent by weight, the thickeners in an amount of about 0.1 to 25% by weight and the care materials in a concentration of about 0.1 to 5.0 percent by weight.

The oxidation dye precursor compositions according to the invention can react weakly acidic, neutral or alkaline according to their composition. They can especially have a pH of 6.0 to 11.5, preferably adjusted with ammonia. The pH however can be adjusted with organic amines, for example monoethanolamine and triethanolamine, or inorganic bases, such as sodium hydroxide and potassium hydroxide. Inorganic or organic acids, for example phosphoric acid, acetic acid, citric acid or tartaric acid, can be used for adjustment of pH in the acid range.

In order to use the oxidation dye precursor composition according to the invention for dyeing hair immediately prior to application to the hair a sufficient amount of this dye precursor composition for dyeing the hair, generally about 60 to 200 g, is mixed with an oxidizing agent. Then the resulting ready-to-apply dye mixture is applied to the hair.

Primarily hydrogen peroxide, or its addition compound with urea, melamine, sodium borate or sodium carbonate, is used as oxidizing agent to develop the hair colors, in the form of a 3- to 12-percent, preferably 6-percent, aqueous solution, however air oxygen can also be considered. If a 6-percent hydrogen peroxide solution is used as oxidizing agent, the weight ratio of oxidation dye precursor composition and oxidizing agent is 5:1 to 1:2, preferably however 1:1. Larger amounts of oxidizing agent are above all used with higher dye compound concentrations in the oxidation dye precursor composition, or if a a more intense bleaching or lightening of the hair color is intended at the same time. The ready-to-apply dye mixture is allowed to act on the hair for about 10 to 45 minutes, preferably 30 minutes, at 15 to 50° C., after being applied to the hair. Then the dye mixture is rinsed from the hair with water and the hair is dried. If necessary the hair may be washed with a shampoo in connection with the rinsing and after-rinsed with a weak organic acid, for example citric or tartaric acid, as needed. Finally the hair is dried.

The oxidation dye precursor compositions containing the substituted 2,5-diamino-1-aminomethylbenzene compounds of formula (I) provide dyed hair colors having outstanding color fastness, especially light fastness, wash fastness, and fastness to rubbing. They provide a broad palette of various color shades and tones, which extend from blond shades to brown, purple, violet up to blue and black color shades according to the type and amounts of their various dye compound ingredients. The very good dyeing properties of the dye precursor compositions according to the invention are characterized by the fact that they can dye gray, chemically undamaged hair without difficulties and with good color coverage or color depth. The compounds of formula I also can be employed to produce intense blue colors on keratin fibers without addition of other dye compounds.

The following examples should illustrate the subject matter of the present invention in detail, without limiting the broad concept of the invention or the claims appended hereinbelow.

EXAMPLES

Process Examples

Example 1

Synthesis of Substitued 2,5-diamino-1-aminomethylbenzene Compounds of Formula (I) (General Synthetic Recipe)

A. Synthesis of 2,5-bis-tert.-butyloxycarbonylaminobromobenzene 15.65 g (0.07 mol) bromo-p-phenylenediamine hydrochloride and 32.7 g (0.15 mol) di-tert-butyl dicarbonate are dissolved in a mixture of 250 ml 2N sodium hydroxide solution and 250 ml trifluorotoluene and the mixture is heated at 45° C. The reaction mixture is stirred for 3 days. Additional 30 g (0.14 mol) di-tert.-butyl dicarbonate are added gradually.

Subsequently the organic layer is separated and the aqueous phase is extracted twice with 100 ml of dichloromethane. The combined extracts are evaporated to form a residue and the residue is taken up in 200 ml of hexane The precipitate is separated by filtration and washed with 50 ml hexane. 18.6 g (82% of theoretical) of 2,5-bis-tert.-butyloxycarbonylaminobromobenzene were obtained with a melting point of 130° C.

B. Synthesis of N-(4-tert.-butyloxycarbonylamino-2-formylphenyl)carbamic Acid-Tert.Butyl Ester 3.3 g (0.01 mol) 2,5-bis-tert.-butyloxycarbonylaminobromobenzene from step A are dissolved in 100 ml of water-free tetrahydrofuran under argon. Gradually 17 ml of a 1.6 molar methyl lithium ether solution (0.03 mol) are added. The reaction mixture is cooled to −20° C. Subsequently 7 ml of 1.5 molar t-butyl lithium solution (0.01 mol) are added gradually. After ending the addition the solution is stirred for 30 minutes at −20° C. Subsequently 1.2 g of dimethylformamide (0.02 mol) are added and the reaction mixture is stirred for an hour at −20° C. After slow heating to room temperature the reaction mixture is hydrolyzed with water and then poured into ether, the aqueous phase is extracted with ether and then the organic phase is dried with magnesium sulfate. The solvent is distilled off in a rotary evaporator and the residue is purified on silica gel with petroleum ether/ethyl acetate (9:1).

C. Synthesis of the Substituted 2,5-diamino-1-aminomethylbenzenes 0.033 g (0.0001 mol) of N-(4-tert.-butyloxycarbonylamino-2-formylphenyl)carbamic acid-tert.butyl ester from step B and 0.00015 mol of a suitable amine are dissolved in 1,2-dichloroethane. Subsequently 0.1 mol of an acetic acid solution (1 m, in 1,2-dichloroethane) and 0.06 g NaBH(OAc)$_3$ (0.0003 mol) are added and the resulting reaction mixture is stirred for 5 to 15 hours. After the reaction has ended the reaction mixture is poured into 10 ml of ethyl acetate, the organic phase is extracted with sodium hydrogen carbonate and then dried with magnesium sulfate. The solvent is distilled off in a rotary evaporator and the residue is purified chromatographically with petroleum ether/ethyl acetate (9:1). The product obtained is heated in 4 ml of ethanol at 50° C. Subsequently 1.5 ml of 2.9 molar ethanolic hydrochloric acid solution are added dropwise to make the hydrochloride. The precipitate is filtered, washed twice with ethanol and then dried.

a. 4-(2,5-diaminobenzylamino)aniline Hydrochloride
  Amine used: 4-tert.-butyloxycarbonylamino-aniline
  Yield: 0.025 g (67% of theory)
  Mass spectrum: MH$^+$ 229 (100)
b. 2-(4-amino-2-methylphenyl)aminomethyl-1,4-diaminobenzene Hydrochloride and 2-(4-amino-3-methylphenyl)aminomethyl-1,4-diaminobenzene Hydrochloride
  Amine used: 4-tert.butyloxycarbonylamino-3-methylaniline and 4-tert.-butyloxycarbonylamino-2-methylaniline
  Yield: 0.025 g (27% of theory)
  Mass spectrum: MH$^+$ 243 (80)
c. 2-(3-aminophenyl)aminomethyl-1,4-diaminobenzene Hydrochloride
  Amine used: 3-tert.-butyloxycarbonylamino-aniline
  Yield: 0.025 g (67% of theory)
  Mass spectrum: MH$^+$ 229 (100)

d. 2-[5-amino-2-(2,5-diaminobenzylamino)phenyl]ethanol Hydrochloride and 2-[2-amino-5-(2,5-diaminobenzylamino)phenyl]ethanol Hydrochloride Amine used: 4-tert.-butyloxycarbonylamino-3-(2-hydroxyethyl)aniline and 4-tert.-butyloxycarbonylamino-2-(2-hydroxyethyl)aniline Yield: 0.025 g (30% of theory)

Mass spectrum: MH$^+$ 273 (100)

e. 2-[4-amino-2-(2,5-diaminobenzylamino)phenoxy]ethanol Hydrochloride

Amine used: 4-tert.butyloxycarbonylamino-2-amino-(2-hydroxy)-ethoxybenzene

Yield: 0.025 g (58% of theory)

Mass spectrum: MH$^+$ 289 (100)

f. 2-(4-dimethylaminophenyl)aminomethyl-1,4-diaminobenzene Hydrochloride

Amine used: 4-amino-N,N-dimethylaniline

Yield. 0.025 g (62% of theory)

Mass spectrum: MH$^+$ 257 (100)

TABLE I

ABBREVIATIONS USED IN EXAMPLES 3 TO 17
Substituted 2,5-diamino-1-aminomethylbenzene(s) of Formula (I)

| | |
|---|---|
| E1a | 4-(2,5-diaminobenzylamino)aniline hydrochloride |
| E1b | 2-(4-amino-2-methylphenyl)aminomethyl-1,4-diaminobenzene hydrochloride/2-(4-amino-3-methylphenyl)aminomethyl-1,4-diaminobenzene hydrochloride |
| E1c | 2-(3-aminophenyl)aminomethyl-1,4-diaminobenzene Hydrochloride |
| E1d | 2-[5-amino-2-(2,5-diaminobenzylamino)phenyl]ethanol hydrochloride/2-[2-amino-5-(2,5-diaminobenzyl-amino)phenyl]ethanol hydrochloride |
| E1e | 2-[4-amino-2-(2,5-diaminobenzylamino)phenoxy]ethanol hydrochloride |
| E1f | 2-(4-dimethylaminophenyl)aminomethyl-1,4-diaminobenzene hydrochloride |
| Developer Substances | |
| E2 | 1,4-diaminobenzene |
| E3 | 2,5-diaminophenylethanol sulfate |
| E4 | 2,5-diaminotoluene sulfate |

TABLE I-continued

ABBREVIATIONS USED IN EXAMPLES 3 TO 17
Substituted 2,5-diamino-1-aminomethylbenzene(s) of Formula (I)

| | |
|---|---|
| Coupler Substances | |
| K13 | 1,3-diamino-4-(2'-hydroxyethoxy)benzene sulfate |
| K22 | 5-amino-2-methylphenol |
| K25 | 1-naphthol |
| K31 | 1,3-dihydroxybenzene |
| Dyestuff | |
| D1 | 2-amino-5-methylphenol |
| D2 | 2-amino-6-methylphenol |
| D5 | 2-amino-6-chloro-4-nitrophenol |

Examples 3 to 11

Hair Dye Precursor Compositions

HAIR DYE SOLUTIONS:

X g 4-(2,5-diaminobenzylamino)aniline hydrochloride (E1a)
U g developer substance E1 to E9 according to the following Table II
Z g dyestuff D according to the following table II
10.0 g potassium oleate (8 percent aqueous solution)
10.0 g ammonia (22 percent aqueous solution)
10.0 g ethanol
0.3 g ascorbic acid
to 100.0 g water 30 g of the above-described hair dye solution are mixed with 30 g of a 6 percent hydrogen peroxide solution immediately prior to application. Subsequently the mixture is applied to bleached hair. After an acting time of 30 minutes at 40° C. the hair is rinsed with water, washed with a commercial shampoo and dried. The resulting dyed hair colors are tabulated in the following Table II.

TABLE II

COMPOSITIONS OF EXAMPLES 3 TO 11 AND DYED HAIR COLORS PRODUCED USING EXAMPLES 3 TO 11*

| Example No./ Dye stuff | 3 | 4 | 5 | 6 | 7 | 8 | 9 | 10 | 11 |
|---|---|---|---|---|---|---|---|---|---|
| E1a | 0.90 | 0.37 | 0.30 | 0.38 | 0.38 | 0.38 | 0.38 | 0.38 | 0.30 |
| E2 | | | | 0.12 | | | | | |
| E3 | | | | | 0.15 | | | | |
| E9 | | | | | | | 0.13 | | |
| D1 | | 0.18 | | 0.18 | 0.18 | 0.18 | 0.06 | 0.18 | 0.30 |
| D2 | | | 0.18 | | | | 0.24 | | |
| D5 | | | | | | | | 0.12 | |
| Color | Deep Blue | Medium Brown | Medium Blond | Black-Brown | Brown | Black-Brown | Medium Brown | Brown | Red-brown |

*Amounts of the dyestuffs are listed in grams.

Examples 12 to 17

Hair Dye Precursor Compositions

| HAIR DYE SOLUTIONS: |
| --- |
| 0.00125 mol substituted 2,5-diamino-1-amionmethylbenzene compound of formula I according to the following Table III (E1a to E1f) |
| 0.00125 mol coupler substance K according to Table III |
| 1.0 g potassium oleate (8 percent aqueous solution) |
| 1.0 g ammonia (22 percent aqueous solution) |
| 1.0 g ethanol |
| 0.3 g ascorbic acid |
| to 100.0 g water |

30 g of the above-described hair dye solution are mixed with 30 g of a 6 percent hydrogen peroxide solution immediately prior to application. Subsequently the mixture is applied to bleached hair. After an acting time of 30 minutes at 40° C. the hair is rinsed with water, washed with a commercial shampoo and dried. The resulting dyed hair colors are tabulated in the following Table III.

TABLE III

DYED HAIR COLORS PRODUCED USING EXEMPLARY HAIR DYE SOLUTIONS 12 TO 17

| Example | Coupler/ Developer | K31 | K13 | K22 | K25 |
| --- | --- | --- | --- | --- | --- |
| 12 | E1a | Blue | Deep blue | Blue | Deep blue |
| 13 | E1b | Violet | Deep blue | Violet | Blue |
| 14 | E1c | Deep blue | Deep blue | Gray-rose | Grey-blue |
| 15 | E1d | Violet | Deep blue | Violet | Violet |
| 16 | E1e | Gray-blue | Gray-blue | Gray-blue | Grey-blue |
| 17 | E1f | Bright Ash Blond | Grey-blue | Purple | Gray-rose |

Example 18

Oxidation Hair Dye Precursor Composition

| | |
| --- | --- |
| 0.32 g | 2,5-diaminotoluene hydrochloride |
| 0.04 g | 5-amino-2-methylphenol |
| 0.09 g | 4-(2,5-diaminobenzylamino)aniline hydrochloride |
| 0.03 g | 3-aminophenol |
| 0.03 g | 1,3-dihydroxybenzene |
| 0.04 g | 1,3-dihydroxy-2-methylbenzene |
| 0.10 g | 4-amino-3-methylphenol |
| 0.20 g | 2-amino-5-methylphenol |
| 0.10 g | 2-amino-6-methylphenol hydrochloride |
| 0.01 g | 4-chloro-N-(2-hydroxyethyl)-2-nitroaniline |
| 0.02 g | 2-amino-4,6-dinitrophenol |
| 0.10 g | 2-chloro-6-(ethylamino)-4-nitrophenol |
| 10.00 g | potassium oleate (8 percent aqueous solution) |
| 10.00 g | ammonia (22 percent aqueous solution) |
| 10.00 g | ethanol |
| 0.30 g | ascorbic acid |
| to 100.0 g | water |

30 g of the above-described hair dye solution are mixed with 30 g of a 6 percent hydrogen peroxide solution immediately prior to application. Subsequently the mixture is applied to bleached hair. After an acting time of 30 minutes at 40° C. the hair is rinsed with water, washed with a commercial shampoo and dried. The resulting dyed hair color was brown.

Example 19

Oxidation Hair Dye Precursor Composition

| | |
| --- | --- |
| 0.32 g | 2,5-diaminophenylethanol sulfate |
| 0.04 g | 5-amino-2-methylphenol |
| 0.05 g | 4-(2,5-diaminobenzylamino)aniline hydrochloride |
| 0.03 g | 3-aminophenol |
| 0.03 g | 1,3-dihydroxybenzene |
| 0.04 g | 1,3-dihydroxy-2-methylbenzene |
| 0.10 g | 4-amino-3-methylphenol |
| 0.20 g | 2-amino-5-methylphenol |
| 0.10 g | 2-amino-6-methylphenol hydrochloride |
| 0.01 g | 4-chloro-N-(2-hydroxyethyl)-2-nitroaniline |
| 0.02 g | 2-amino-4,6-dinitrophenol |
| 0.10 g | 2-chloro-6-(ethylamino)-4-nitrophenol |
| 10.00 g | potassium oleate (8 percent aqueous solution) |
| 10.00 g | ammonia (22 percent aqueous solution) |
| 10.00 g | ethanol |
| 0.30 g | ascorbic acid |
| to 100.0 g | water |

30 g of the above-described hair dye solution are mixed with 30 g of a 6 percent hydrogen peroxide solution immediately prior to application. Subsequently the mixture is applied to bleached hair. After an acting time of 30 minutes at 40° C. the hair is rinsed with water, washed with a commercial shampoo and dried. The resulting dyed hair color was brown.

All percentages given herein are percentages by weight, unless otherwise indicated.

The disclosure in German Patent Application 199 61 274.9 of Dec. 18, 1999 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in substituted 2,5-diamino-1-aminomethylbenzene compounds and oxidation dye precursor compositions for dyeing keratin fibers, especially human hair, containing these compounds, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A substituted 2,5-diamino-1-aminomethylbenzene compound of formula (I), or a physiologically compatible water-soluble salt thereof,

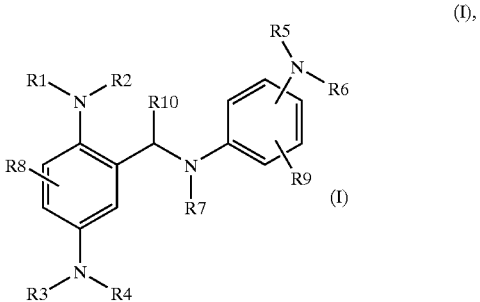

wherein R1, R2, R3, R4, R5, R6 and R7, independently of each other, each represent hydrogen, a $C_1$- to $C_6$-alkyl group, a $C_1$- to $C_4$-hydroxyalkyl group, a $C_2$- to $C_4$-dihydroxyalkyl group or a $C_1$- to $C_4$-alkoxy-($C_1$- to $C_2$-)alkyl group or at least one pair selected from the group consisting of R1 and R2; R3 and R4; and R5 and R6 together with the N atom form a four-member to eight-member aliphatic ring, with the proviso that at least two of said R1 to R6 each represent said hydrogen;

R8 represents hydrogen, a halogen atom, a $C_1$- to $C_4$-alkyl group, a $C_1$- to $C_4$-hydroxyalkyl group or a $C_1$- to $C_4$-alkoxy group;

R9 represents hydrogen, a halogen atom, a cyano group, a hydroxy group, a $C_1$- to $C_4$-alkoxy group, a $C_1$- to $C_4$-hydroxyalkoxy group, a $C_1$- to $C_6$-alkyl group, a $C_1$- to $C_4$-alkylthioether group, a mercapto group, an amino group, a $C_1$- to $C_4$-alkylamino group, a $C_1$- to $C_4$-hydroxyalkylamino group, a di($C_1$- to $C_4$-alkyl) amino group, a di($C_1$- to $C_4$-hydroxyalkyl)amino group, a {dihydroxy($C_2$- to $C_4$)-alkyl}amino group, a ($C_1$- to $C_4$-hydroxyalkyl)-$C_1$–$C_4$-alkylamino group, a trifluoromethane group, a $C_1$–$C_4$-hydroxyalkyl group or a $C_3$–$C_4$ dihydroxyalkyl group; and R10 represents hydrogen or a $C_1$- to $C_6$-alkyl group.

2. The substituted 2,5-diamino-1-aminomethylbenzene compound as defined in claim 1, wherein at least one of said R5 to R10 represents said hydrogen.

3. The substituted 2,5-diamino-1-aminomethylbenzene compound as defined in claim 1 or 2, wherein each of said R1, R2, R3 and R4 represents said hydrogen.

4. The substituted 2,5-diamino-1-aminomethylbenzene compound as defined in claim 1, wherein said R7, R8, R9 and R10 each represent said hydrogen and wherein said R5 and R6, independently of each other, each represent said hydrogen, said $C_1$- to $C_6$-alkyl group, said $C_1$- to $C_4$-hydroxyalkyl group or said $C_2$- to $C_4$-dihydroxyalkyl group, or said R5 and R6 together with the N atom forms said four-member aliphatic ring.

5. A substituted 2,5-diamino-1-aminomethylbenzene compound selected from the group consisting of 2-((2-amino-phenylamino)-methyl)-1,4-diaminobenzene; 2-((3-aminophenyl-amino)-methyl)-1,4-diaminobenzene; 2-((4-aminophenylamino)methyl)-1,4-diaminobenzene; 2-((4-bis (2-hydroxyethyl)aminophenylamino)-methyl)-1,4-diaminobenzene; 2-((4-dimethylamino-phenylamino) methyl)-1,4-diamino-benzene; $N^1,N^1$-bis(hydroxyethyl)-2-((3-aminophenylamino)-methyl)-1,4-diaminobenzene; $N^1,N^1$-bis(hydroxyethyl)-2-((4-amino-phenylamino)-methyl)-1,4-diaminobenzene, $N^1,N^1$-bis(hydroxyethyl)-2-((4-bis(2-hydroxyethyl)amino-phenylamino)-methyl)-1,4-diaminobenzene; $N^1$-dihydroxypropyl-2-((4-aminophenylamino)-methyl)-1,4-diaminobenzene; $N^1$-dihydroxypropyl-2-((4-bis(2-hydroxyethyl)amino-phenylamino)-methyl)-1,4-diaminobenzene; $N^1$-dihydroxypropyl-2-((4-dimethylaminophenylamino)-methyl)-1,4-diaminobenzene; $N^4,N^4$-bis(hydroxyethyl)-2-((3-aminophenylamino)-methyl)-1,4-diaminobenzene; $N^4$, $N^4$-bis(hydroxyethyl)-2-((4-aminophenylamino)-methyl)-1, 4-diaminobenzene; $N^4$, $N^4$-bis(hydroxy-ethyl)-2-((4-bis(2-hydroxyethyl)-amino-phenylamino)-methyl)-1,4-diaminobenzene; $N^4$, $N^4$-bis(hydroxyethyl)-2-((4-dimethylamino-phenyl-amino)-methyl)-1,4-diaminobenzene; $N^4$-dihydroxypropyl-2-((4-amino-phenylamino)-methyl)-1,4-diaminobenzene; $N^4$-dihydroxypropyl-2-((4-bis(2-hydroxy-ethyl)amino-phenylamino)-methyl)-1,4-diaminobenzene; $N^4$-dihydroxypropyl-2-((4-dimethylamino-phenylamino)-methyl)-1,4-diamino-benzene; 2-((2-(2-hydroxyethyl) aminophenylamino)-methyl)-1,4-diamino-benzene; 2-((2-(pyrrolidin-1-yl)-phenylamino)-methyl)-1,4-diaminobenzene; 2-((2-dihydroxypropylamino-phenylamino)-methyl)-1,4-diaminobenzene; 2-((2-methylamino-phenylamino)-methyl)-1,4-diaminobenzene; 2-((3-(2-hydroxyethyl)-amino-phenylamino)-methyl)-1,4-diaminobenzene; 2-((3-(pyrrolidin-1-yl)-phenylamino)-methyl)-1,4-diaminobenzene; 2-((3-dihydroxypropylamino-phenylamino)-methyl)-1,4-diaminobenzene; 2-((3-methylamino-phenylamino)-methyl)-1,4-diaminobenzene; 2-((4-(2-hydroxyethyl)amino-phenylamino)-methyl)-1,4-diaminobenzene; 2-((4-(pyrrolidin-1-yl)-phenylamino)-methyl)-1,4-diaminobenzene; 2-((4-dihydroxypropylamino-phenylamino)-methyl)-1,4-diaminobenzene; 2-((4-methylamino-phenylamino)-methyl)-1,4-diamino-benzene; 2-((2-(2-hydroxyethyl)-4-amino-phenylamino) methyl)-1,4-diamino-benzene, 2-((2-(2-hydroxyethyl)-4-bis(2-hydroxyethyl)-amino-phenylamino)-methyl)-1,4-diaminobenzene; 2-((2-chloro-4-amino-phenylamino)-methyl)-1,4-diaminobenzene; 2-((2-chloro-4-bis(2-hydroxyethyl)-amino-phenylamino)-methyl)-1,4-diaminobenzene; 2-((2-methoxy-4-amino-phenylamino)-methyl)-1,4-diaminobenzene; 2-((2-methoxy-4-bis(2-hydroxyethyl)-amino-phenylamino)-methyl)-1,4-diaminobenzene; 2-((2-methyl-4-amino-phenylamino)-methyl)-1,4-diaminobenzene; 2-((2-methyl-4-bis(2-hydroxyethyl)amino-phenylamino)-methyl)-1,4-diaminobenzene; 2-((3-(2-hydroxyethyl)-4-amino-phenylamino)-methyl)-1,4-diaminobenzene; 2-((3-(2-hydroxyethyl)-4-bis(2-hydroxyethyl)amino-phenylamino)-methyl)-1,4-diaminobenzene; 2-((3-chloro-4-amino-phenylamino)-methyl)-1,4-diaminobenzene; 2-((3-chloro-4-bis(2-hydroxyethyl)amino-phenylamino)-methyl)-1,4-diaminobenzene; 2-((3-methoxy-4-amino-phenylamino)-methyl)-1,4-diaminobenzene; 2-((3-methoxy-4-bis(2-hydroxyethyl)amino-phenylamino)-methyl)-1,4-diaminobenzene; 2-((3-methyl-4-amino-phenylamino)-methyl)-1,4-diaminobenzene; 2-((3-methyl-4-bis(2-hydroxyethyl)amino-phenylamino)-methyl)-1,4-diaminobenzene; 2-((4-(2-hydroxyethoxy)-3-amino-phenylamino)-methyl)-1,4-diaminobenzene; 2-((4-(2-hydroxyethoxy)-3-bis(2-hydroxyethyl)amino-phenyl amino)-methyl)-1,4-diaminobenzene; 2-((4-(2-hydroxyethyl)-3-amino-phenylamino)-methyl)-1,4-diaminobenzene and 2-((4-(2-hydroxyethyl)-3-bis(2-hydroxyethyl)-amino-phenylamino)-methyl)-1,4-diaminobenzene.

6. An oxidation dye precursor composition for dyeing keratin fibers, said oxidation dye precursor composition containing at least one substituted 2,5-diamino-1-aminomethylbenzene compound of formula (I), or a physiologically compatible water-soluble salt thereof,

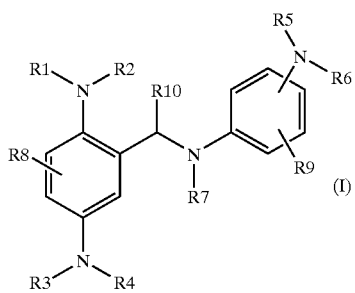

wherein R1, R2, R3, R4, R5, R6 and R7, independently of each other, each represent hydrogen, a $C_1$- to $C_6$-alkyl group, a $C_1$- to $C_4$-hydroxyalkyl group, a $C_2$- to $C_4$-dihydroxyalkyl group or a $C_1$- to $C_4$-alkoxy-($C_1$- to $C_2$-)alkyl group or at least one pair selected from the group consisting of R1 and R2; R3 and R4; and R5 and R6 together with the N atom form a four-member to eight-member aliphatic ring, with the proviso that at least two of said R1 to R6 each represent said hydrogen;

R8 represents hydrogen, a halogen atom, a $C_1$- to $C_4$-alkyl group, a $C_1$- to $C_4$-hydroxyalkyl group or a $C_1$- to $C_4$-alkoxy group;

R9 represents hydrogen, a halogen atom, a cyano group, a hydroxy group, a $C_1$- to $C_4$-alkoxy group, a $C_1$- to $C_4$-hydroxyalkoxy group, a $C_1$- to $C_6$-alkyl group, a $C_1$- to $C_4$-alkylthioether group, a mercapto group, an amino group, a $C_1$- to $C_4$-alkylamino group, a $C_1$- to $C_4$-hydroxyalkylamino group, a di($C_1$- to $C_4$-alkyl) amino group, a di($C_1$- to $C_4$-hydroxyalkyl)amino group, a {dihydroxy($C_2$- to $C_4$)-alkyl}amino group, a ($C_1$- to $C_4$-hydroxyalkyl)-$C_1$–$C_4$-alkylamino group, a trifluoromethane group, a $C_1$–$C_4$-hydroxyalkyl group or a $C_3$–$C_4$ dihydroxyalkyl group; and R10 represents hydrogen or a $C_1$- to $C_6$-alkyl group.

7. The oxidation dye precursor composition as defined in claim 6, containing from 0.005 to 20 percent by weight of said at least one substituted 2,5-diamino-1-aminomethylbenzene compound of the formula (I), or said physiologically compatible water-soluble salt thereof.

8. The oxidation dye precursor composition as defined in claim 6 or 7, further comprising at least one additional dyestuff selected from the group consisting of developer substances, coupler substances, 2-aminophenol, 2-amino-6-methylphenol and direct-dyeing dye compounds.

* * * * *